(12) United States Patent
Gallop et al.

(10) Patent No.: US 10,260,031 B2
(45) Date of Patent: Apr. 16, 2019

(54) OPTIMIZED DEWATERING PROCESS FOR AN AGRICULTURAL PRODUCTION FACILITY

(71) Applicant: ICM, Inc., Colwich, KS (US)

(72) Inventors: Charles C. Gallop, Gower, MO (US); Kurt A. Dieker, Wichita, KS (US)

(73) Assignee: ICM, Inc., Colwich, KS (US)

( * ) Notice: Subject to any disclaimer, the term of this patent is extended or adjusted under 35 U.S.C. 154(b) by 322 days.

(21) Appl. No.: 14/557,175

(22) Filed: Dec. 1, 2014

(65) Prior Publication Data

US 2015/0152371 A1 Jun. 4, 2015

Related U.S. Application Data

(60) Provisional application No. 61/910,896, filed on Dec. 2, 2013.

(51) Int. Cl.
*C12F 3/10* (2006.01)
*B01D 33/11* (2006.01)

(52) U.S. Cl.
CPC ............... *C12F 3/10* (2013.01); *B01D 33/11* (2013.01)

(58) Field of Classification Search
CPC ... C12F 3/10; C12F 3/00; B01D 33/15; B01D 33/00; B01D 33/11; B01D 29/01; B01D 29/00; B01D 33/06; C12P 7/06; C12P 7/04; C12P 7/02; C12P 7/00; C08B 30/044; C08B 30/42; C08B 30/04; C08B 30/00; Y02E 50/17; Y02E 50/10; Y02E 50/00

See application file for complete search history.

(56) References Cited

U.S. PATENT DOCUMENTS

| 6,375,853 | B1 | 4/2002 | Yoon |
| 7,691,259 | B2 | 4/2010 | Freeman et al. |
| 2006/0006116 | A1* | 1/2006 | Scheimann et al. .......... 210/728 |

(Continued)

FOREIGN PATENT DOCUMENTS

| CA | 2827146 A1 | 11/2013 |
| WO | WO-9400219 A1 | 1/1994 |
| WO | WO-2015084740 A1 | 6/2015 |

OTHER PUBLICATIONS

"EPA Proposes 2014 Renewable Fuel Standards, 2015 Biomass-Based Diesel Volume", [online]. Retrieved from the Internet: <URL: http://www.epa.gov/otaq/fuels/renewablefuels/documents/420f13048.pdf>, (Nov. 2013), 4 pgs.

(Continued)

*Primary Examiner* — David C Mellon
*Assistant Examiner* — Liam Royce
(74) *Attorney, Agent, or Firm* — Schwegman Lundberg & Woessner, P.A.

(57) ABSTRACT

This disclosure describes techniques to optimize dewatering process in a production facility. A process separates components in a mixture by using a separation device and a dewatering device. The process receives the mixture of liquids and solids, and separates out suspended solids from the mixture of liquids and solids by using the separation device, wherein a liquid with insoluble solids stream is created. The process dewaters the liquid with insoluble solids stream by using the dewatering device to produce a liquid with small particles stream and insoluble solids having particle sizes that are greater than about 20 microns to about 1000 microns.

17 Claims, 11 Drawing Sheets

(56) References Cited

U.S. PATENT DOCUMENTS

2007/0254089 A1* 11/2007 Hickey et al. ................ 426/624
2008/0257821 A1    10/2008 Jump et al.
2010/0012596 A1*  1/2010 Lee .............................. 210/771
2012/0244590 A1*  9/2012 Lee .............................. 435/161
2013/0264264 A1* 10/2013 Lehoux ............... B01D 33/009
                                                       210/231

OTHER PUBLICATIONS

International Application Serial No. PCT/US2014/067964, International Search Report dated Mar. 26, 2015, 3 pgs.
International Application Serial No. PCT/US2014/067964, Written Opinion dated Mar. 26, 2015, 7 pgs.

* cited by examiner

OPTIMIZED DEWATERING PROCESS FOR AN AGRICULTURAL PRODUCTION FACILITY

CLAIM OF PRIORITY

This patent application claims the benefit of priority of U.S. Provisional Patent Application Ser. No. 61/910,896, filed on Dec. 2, 2013, which is hereby incorporated by reference herein in its entirety.

TECHNICAL FIELD

The subject matter of this disclosure relates to methods of optimizing dewatering insoluble solids in a production facility. In particular, the subject matter is directed to using a dewatering device to remove liquids from insoluble solids, to recover components, to reduce amount of energy needed for downstream processing, to reduce greenhouse gas and/or carbon emissions, and to increase overall efficiency of a process.

BACKGROUND

The United States relies on imported petroleum to meet the needs of transportation fuel. To reduce dependence on the imported petroleum, the Environmental Protection Agency (EPA) set standards for a Renewable Fuel Standard (RFS2) program each year. See, United States Environmental Protection Agency, Office of Transportation and Air Quality, "EPA Proposes 2014 Renewable Fuel Standards, 2015 Biomass -Based Diesel Volume," November 2013 Regulatory Announcement. The RFS2 includes a mandate to blend renewable fuels into transportation fuel, which ensures the continued growth of renewable fuels. The RFS2proposes annual standards for cellulosic biofuel, biomass-based diesel, advanced biofuel, and total renewable fuel that apply to gasoline and diesel. The proposal is 17 million gallons of cellulosic biofuels, 1.28 billion gallons of biomass-based diesel, 2.0-2.5 billion gallons of advanced biofuel, and 15-15.5 billion gallons of renewable fuel to be produced and for consumption in 2014.

Meanwhile, efforts have been undergoing to reduce travel demand, to improve vehicle efficiency, and to switch to cleaner, lower-carbon fuels. These efforts have focused on establishing a national low carbon fuel standard (LCFS) together, or in place of the RFS2. The LCFS includes all types of transporatation fuels (i.e., electricity, natural gas, hydogen, and biofuels), requires reducing a fuel's average life-cycle gas house gas (GHG) emissions or carbon-intensity (CI) over a certain period of time, and stimulates innovation by rewarding production facilities that reduce GHG or carbon emissions at every step. Production facilities can reduce CI of fuels by selling more low-carbon fuels, reducing the CI of fossil fuels, improving efficiencies, reducing carbon footprints, capturing and sequesting carbon, and/or purchasing credits from other producers who are able to supply low-carbon fuels at lower prices. California and some countries have adopted the LCFS policy. Other states and regions in the U.S. are considering adopting a LCFS policy similar to California's model.

A national LCFS would affect the economy and environment. These effects may be based on cost and availability of low-carbon fuels, GHG timeline reduction, and creation of a credit system. Advantages of incorporating LCFS to RFS2 are to reduce transportation fuel consumption and lower fuel prices, lower crop prices by shifting towarding cellulosic feedstocks, and reduce GHG or carbon emmisions significantly domestically and globablly. Thus, production facilities are seeking ways to implement LCFS on their own.

Since production facilities produce emissions, methods to implement LCFS include finding more efficient technologies. For instance, there are known techniques to separate solids from liquids in process streams. However, these techniques are not very efficient. For instance, one method uses heat and/or a centrifuge with the process streams to separate and to recover various components. Problems are that the centrifuge may not separate components, based on density differential and may not adequately separate solids from liquids in the process streams, is expensive to purchase and to operate, requires frequent maintenance and repair, and requires a higher skill set to operate and to maintain. Also, the solids have high moisture content, which drives up operating costs to transport and to dry the solids downstream. Plus, these pieces of equipment create emissions from the plants. Other types of equipment have been attempted for solids-liquids separation, but tend to drive up capital and operating costs.

Accordingly, there is a need for improved methods for optimization of dewatering insoluble solids in a more efficient manner by reducing GHG or carbon emissions, decreasing the amount of energy used for downstream processing, reducing operating costs, and/or reducing capital costs.

SUMMARY

This disclosure describes optimization of dewatering insoluble solids, recovering components, enhancing solid-liquid separation, and improving overall efficiency in a production facility. This disclosure helps to reduce an amount of energy used for downstream processing, which in turn reduces GHG or carbon emissions, and reduce operating costs and/or reduce capital costs, which in turn may lower biofuel costs.

In an embodiment for reducing an amount of energy needed for processing streams, a process separates components in a mixture by using a separation device and a dewatering device. The process receives a mixture of liquids and solids, and separates out suspended solids from the mixture of liquids and solids by using the separation device, and creating a liquid with insoluble solids stream. The process further dewaters the liquid with insoluble solids stream by using a dewatering device to produce 1) a liquid with small particles stream and 2) insoluble solids, which have solids content that are about 10% to about 70% solids.

In another embodiment for reducing an amount of energy needed for processing streams, a process separates components in a mixture by using a dewatering device. The process receives liquids and solids in a process stream from a production facility, and dewaters the liquids and solids in the process stream by using a dewatering device. The process produces 1) a liquid with small particles stream and 2) insoluble solids having solids content greater than about 25% solids.

In yet another embodiment, a method receives liquids and solids in a process stream up to about 38% solids content, dewaters the liquids and solids in the process stream with a dewatering device, and produces 1) a liquid with small particles stream having up to about 20% solids content and 2) insoluble solids having less than about 55% solids content.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Other aspects and advantages of the claimed subject matter will be apparent from the following Detailed Description of the embodiments and the accompanying figures.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items. The features illustrated in the figures are not necessarily drawn to scale, and features of one embodiment may be employed with other embodiments as the skilled artisan would recognize, even if not explicitly stated herein.

DETAILED DESCRIPTION

Overview

Figure 1:
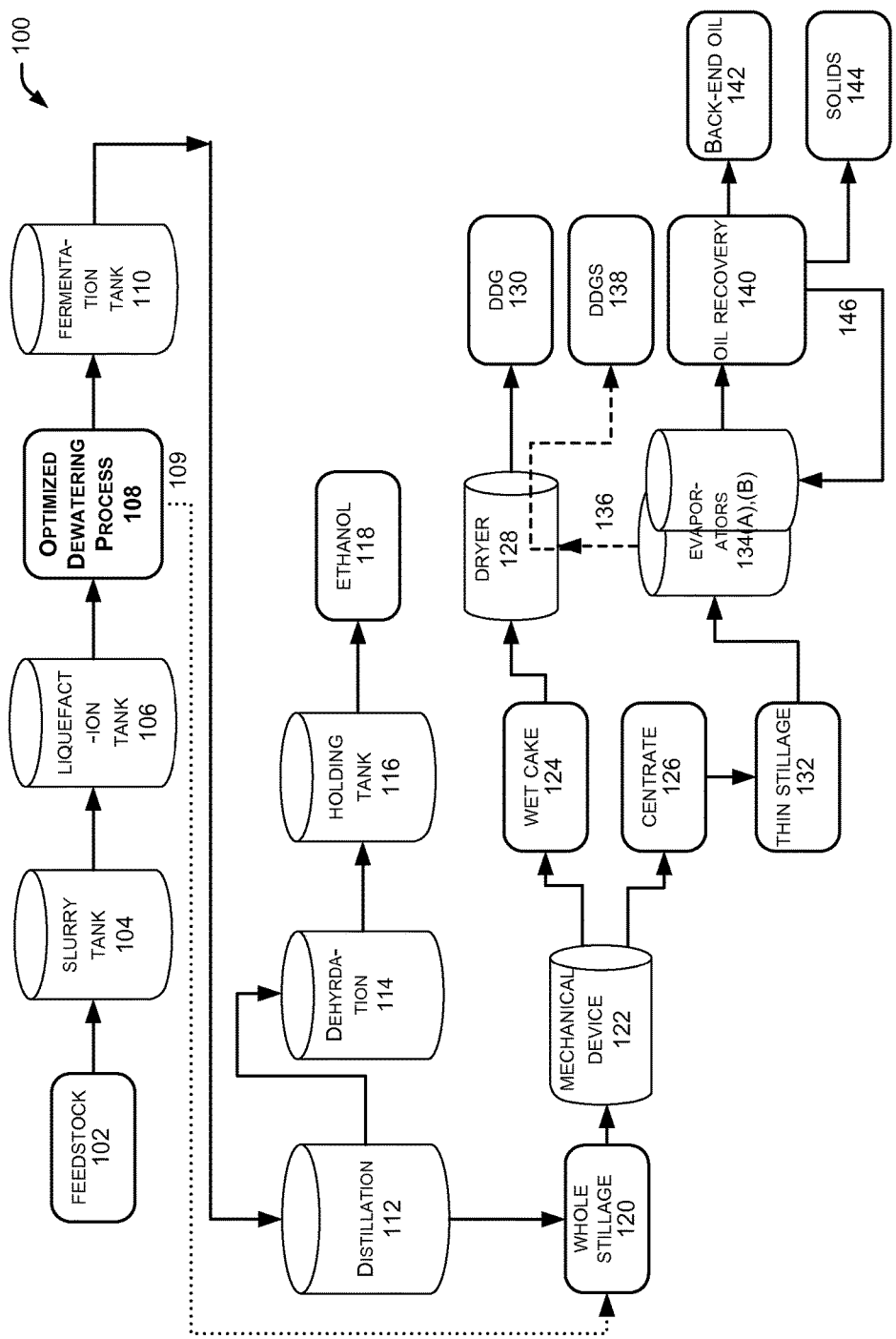
FIG. 1 illustrates an example environment for an optimized dewatering process in a front end of a production facility.

The Detailed Description explains embodiments of the subject matter and the various features and advantageous details more fully with reference to non-limiting embodiments and examples that are described and/or illustrated in the accompanying figures and detailed in the following attached description. Descriptions of well-known components and processing techniques may be omitted so as to not unnecessarily obscure the embodiments of the subject matter. The examples used herein are intended merely to facilitate an understanding of ways in which the subject matter may be practiced and to further enable those of skill in the art to practice the embodiments of the subject matter. Accordingly, the examples, the embodiments, and the figures herein should not be construed as limiting the scope of the subject matter.

This disclosure describes environments and techniques for an optimized dewatering process by separating liquids from insoluble solids in a mixture or process stream obtained from the production facility. For instance, the production facility may include, but is not limited to, biofuels, alcohol, animal feed, oil, biodiesel, pulp and paper, textile, chemical industry, and other fields. Removal of liquids from the insoluble solids will increase the concentration of solids in downstream process streams, enhance more efficient solid-liquid separation to recover components, and allow more efficient drying for downstream processing.

The optimized dewatering process presents opportunities to reduce GHG or carbon emissions by providing methods to produce insoluble solids having less moisture or higher solids content than conventional methods. With the insoluble solids having less moisture or higher solids content, the process may reduce energy usage downstream for drying and/or evaporating and reduce operating costs while improving efficiency in the production facility. For instance, the downstream processing uses electricity and natural gas to operate the evaporators and dryers, which generate emissions into the atmosphere. With the optimized dewatering process, the amount of electricity and natural gas to operate the evaporators and dryers would be reduced and so would the amount of emissions.

Furthermore, the optimized dewatering process provides biofuels that have a lower carbon intensity than conventional biofuels or hydrocarbon fuels. For instance, the LCFS establishes carbon intensity standard measured in grams $CO_2$ equivalent per mega-joule of fuel energy ($gCO_2e/MJ$) over a certain period of time. The production facilities supply an accounting of net fuel emissions per unit of fuel energy. It appears that the optimized dewatering process operates within regulatory agencies that can quantify environmental benefits or associate a biofuel or a tradable credit. Thus, there are economic incentives, environmental benefits, other advantages, and benefits to using the optimized dewatering process that provide a more energy efficient industrial process.

In an embodiment for reducing an amount of energy needed for processing streams, a process separates components in a mixture by using a separation device and a dewatering device. The process receives the mixture of liquids and solids, and separates out suspended solids from the mixture of liquids and solids by using the separation device, wherein a liquid with insoluble solids stream is created. The process dewaters the liquid with insoluble solids stream by using the dewatering device to produce 1) a liquid with small particles stream and 2) insoluble solids ranging from about 10% to about 70% solids content.

In another embodiment for reducing an amount of energy needed for processing streams, a process separates components in a process stream by using a dewatering device. The process receives the liquids and solids in the process stream, and dewaters the liquids and solids in the process stream by using the dewatering device. The process produces 1) a liquid with small particles stream and 2) insoluble solids, greater than about 25% solids content.

The terms, dewater and dewatering, are used to indicate removal of liquids from solids. The liquids with small particles include water, starch, gluten, other components, soluble solids, and fine particles. The terms, insoluble solids, are used to indicate solids that do not dissolve and contain moisture.

Embodiments of the optimized dewatering process are shown for illustration purposes in the dry grind process and the wet mill process. The optimized dewatering process may be implemented in the different fields as discussed above.

While aspects of described techniques can be implemented in any number of different environments, and/or configurations, implementations are described in the context of the following example processes.

Illustrative Environments

FIGS. 1-4 and 9-11 are flow diagrams showing example environments that may be used with the optimized dewatering process. The process may be performed using a combination of different environments and/or types of equipment. Any number of the described environments, processes or types of equipment may be combined in any order to implement the method, or an alternate method. Moreover, it is also possible for one or more of the provided steps or pieces of equipment to be omitted.

FIG. 1 illustrates an example of a process 100 implementing a series of operations in the dry grind mill of an alcohol production facility. The process 100 in the dry grind mill may operate in a continuous manner. In other implementations, the process 100 may operate in a batch process or a combination of batch and continuous processes.

The process 100 may receive feedstock of a grain that includes, but is not limited to, barley, beets, cassava, corn, cellulosic feedstock, grain, milo, oats, potatoes, rice, rye, sorghum grain, triticale, sweet potatoes, lignocellulosic biomass, wheat, and the like, or pulp. Lignocellulosic biomass may include corn fiber, corn stover, corn cobs, cereal straws, sugarcane bagasse and dedicated energy crops, which are mostly composed of fast growing tall, woody grasses, including, but not limited to, switch grass, energy/forage sorghum, miscanthus, and the like. Also, the feedstock may further include, grain fractions or by-products as produced by industry, such as hominy, wheat middlings, corn gluten feed, Distillers Dried Grains with Solubles, and the like. The feedstock may include, an individual type, a combined feedstock of two types, of multiple types, or any combination or blend of the above grains. The feedstock may include, but is not limited to, one to four different types combined in various percentage ranges. The feedstock may be converted into different products and co-products that may include, but is not limited to, germ to be extracted for oil, food grade protein meal for high protein animal feed, and starch-based and fermentation-based products such as ethanol, syrup, food, and industrial starch. The feedstock may be processed for other applications that include, but are not limited to, producing chemicals for use in other applications, plastics, and other fields.

For brevity purposes, the process 100 of using a single stream of feedstock will be described with reference to FIG. 1. As an example, corn may be used as a single feedstock in the dry grind process. Corn may be broken down into its major components of endosperm, germ, bran, and tip cap. Each of these major components may be further broken down to their smaller components. The endosperm, the germ, the bran, and the tip cap each contains varying amounts of starch, protein, oil, fiber, ash, sugars, etc. For instance, the amounts of the components in corn may include, but are not limited to, about 70 to 74% starch, about 7 to 9% protein, about 3 to 4% oil, about 7 to 9% fiber, about 1 to 2% ash, about 1 to 2% sugars, and others.

One skilled in the art understands that inspecting and cleaning of the corn occurs initially. At feedstock 102, the process 100 initially grinds the feedstock 102 into a meal, a powder, or a flour to achieve an appropriate particle size. The process 100 may grind the feedstock 102 by using hammer mills or roller mills. This grinding serves to break an outer coating of the corn kernel and increases a surface area to expose starch for penetration of water in cooking.

In an embodiment, the process 100 uses a hammer mill (not shown). The hammer mill is a cylindrical grinding chamber with a rotating drum, flat metal bars, and a screen. The screen size may be, but is not limited to, 4/64 to 12/64 inch hole sizes. An example hammer mill may have screen openings that are sized 7/64 inch, or about 2.78 millimeters (mm) to create fine particles that are sized about 0.5 to about 2-3 mm.

In another embodiment, the process 100 uses a roller mill (not shown). The roller mill receives the feedstock 102, passes the feedstock 102 between two or more rolls or wheels, and crushes the feedstock 102 in the process 100. One roll may be fixed in position while the other roll may be moved further or closer towards the stationary roll. The roll surfaces may be grooved to help in shearing and disintegration of the corn. The example rolls may be about 9 to about 12 inches (23 to 30.5 cm) in diameter, with a ratio of length to diameter that may be about 4:1. The fine particles may be sized about 0.5 to about 2-3 mm.

At slurry tank 104, the process 100 adds water, backset, and enzymes to the feedstock 102 that has been ground to create a slurry. In an example, the process 100 adds a liquefying enzyme, such as alpha-amylase. The alpha-amylase enzyme hydrolyzes and breaks starch polymer into short sections, dextrins, which are a mix of oligosaccharides. The process 100 maintains a temperature between about 60° C. to about 100° C. (about 140° F. to about 212° F., about 333 K to about 373 K) in the slurry tank 104 to cause the starch to gelatinize and a residence time of about 30 to about 60 minutes to convert insoluble starch in the slurry to soluble starch. The slurry may have suspended solids content of about 26 to about 40%, which includes starch, fiber, protein, and oil. Other components in the slurry tank 104 may include, grit, salts, and the like, as is commonly present on raw incoming grain from agricultural production, as well as recycle waters that contain acids, bases, salts, yeast, and enzymes. The process 100 adjusts the pH of the slurry to about 4.5 to 6.0 (depending on enzyme type) in the slurry tank 104.

In an embodiment, the slurry may be heated to further reduce viscosity of the ground grain. In some embodiments, there may be two or more slurry tanks used for an additional residence time and a viscosity reduction.

In an embodiment, the process 100 pumps the slurry to jet cookers (not shown) to cook the slurry. Jet cooking may occur at elevated temperatures and pressures. For example, jet cooking may be performed at a temperature of about 104 to about 150° C. (about 220 to about 302° F.) and at an absolute pressure of about 1.0 to about 6.0 kg/cm$^2$ (about 15 to 85 lbs/in$^2$) for about five minutes. Jet cooking is another method to gelatinize the starch.

At liquefaction tank 106, the process 100 converts the slurry to mash. The process 100 uses a temperature range of about 80 to about 150° C. (about 176 to about 302° F., about 353 K to about 423 K) to hydrolyze the gelatinized starch into maltodextrins and oligosaccharides to produce a liquefied mash. Here, the process 100 produces a mash stream, which has about 26 to about 40% total solids content. The mash may have suspended solids content that includes protein, oil, fiber, grit, and the like. In embodiments, one or more liquefaction tanks may be used in the process 100.

The process 100 may add another enzyme, such as glucoamylase in the liquefaction tank 106 to break down the dextrins into simple sugars. Specifically, the glucoamylase enzyme breaks the short sections into individual glucose.

The process 100 may add the glucoamylase enzyme at about 60° C. (about 140° F., about 333 K) before fermentation starts, known as saccharification, or at the start of a fermentation process. In an embodiment, the process 100 further adjusts the pH to about 5.0 or lower in the liquefaction tank 106. In another embodiment, saccharification and fermentation may also occur simultaneously.

For illustrative purposes in FIG. 1, an optimized dewatering process 108 is presented at a high level in a front end of the production facility. Details of embodiments of the optimized dewatering process 108 will be discussed later with reference to FIGS. 5-8. The optimized dewatering process 108 may be included with any process as part of the dry grind process or any type of process in a production facility. Specifically, the optimized dewatering process 108 helps to remove liquids from insoluble solids, improve the separation of solids from liquids, increase the amount of product and co-products produced per bushel and to reduce GHG or carbon emissions.

At liquefaction tank 106, the optimized dewatering process 108 obtains the process stream or a mixture from the slurry tank 104. In other embodiments, the optimized dewatering process may obtain the process stream or mixture as slurry from a slurry tank, from a jet cooker, from a first liquefaction tank, from a second liquefaction tank, or after a pretreatment process in cellulosic production facility. In an embodiment, a stream 109 from the optimized dewatering process 108 goes to whole stillage 120, bypassing fermentation tank 110. In another embodiment, the stream 109 may bypass fermentation tank and whole stillage 120, going directly to mechanical device 122. In yet another embodiment, the stream 109 may bypass fermentation tank 110 and whole stillage 120, going directly to wet cake 124.

At fermentation tank 110, the process 100 sends a liquid with small particles stream from the optimized dewatering process 108 to the fermentation tank. The process 100 adds a microorganism to the mash for fermentation in the fermentation tank 110. The process 100 may use a common strain of microorganism, such as *Saccharomyces cerevisae* to convert the simple sugars (i.e., maltose and glucose) into alcohol with solids and liquids, $CO_2$, and heat. The process 100 may use a residence time in the fermentation tank 110 as long as about 50 to about 60 hours. However, variables such as a microorganism strain being used, a rate of enzyme addition, a temperature for fermentation, a targeted alcohol concentration, and the like, may affect fermentation time. In embodiments, one or more fermentation tanks may be used in the process 100.

The process 100 creates alcohol, solids, and liquids through fermentation in the fermentation tank 110. Once completed, the mash is commonly referred to as beer, which may contain about 10 to about 20% alcohol, plus soluble and insoluble solids from the grain components, microorganism metabolites, and microorganism bodies. The microorganism may be recycled in a microorganism recycling step, which is an option.

The part of the process 100 that occurs prior to distillation 112 may be referred to as the "front end", and the part of the process 100 that occurs after distillation 112 may be referred to as the "back end".

Turning to distillation 112, the process 100 distills the beer to separate the alcohol from the non-fermentable components, solids and the liquids by using a distillation process, which may include one or more distillation columns, beer columns, and the like. The process 100 pumps the beer through distillation 112, which is boiled to vaporize the alcohol or produce concentrated stillage. The process 100 condenses the alcohol vapor in distillation 112 where liquid alcohol exits through a top portion of the distillation 112 at about 88 to about 95% purity, which is about 190 proof. In embodiments, the distillation columns and/or beer columns may be in series or in parallel.

At dehydration 114, the process 100 removes any moisture from the 190 proof alcohol by going through dehydration. The dehydration 114 may include one or more drying column(s) packed with molecular sieve media to yield a product of nearly 100% alcohol, which is 200 proof alcohol.

At holding tank 116, the process 100 adds a denaturant to the alcohol. Thus, the alcohol is not meant for drinking but to be used for motor fuel purposes. At 118, an example product that may be produced is ethanol, to be used as fuel or fuel additive for motor fuel purposes.

At 120, the water-rich product remaining from the distillation 112 is commonly referred to as whole stillage. The components in the whole stillage 120 may include components such as, suspended solids, dissolved solids, and water. For instance, the components include oil, protein, fiber, minerals, acids, bases, recycled yeast, and the like. Whole stillage 120 falls to the bottom of the distillation 112 and passes through a mechanical device 122.

The mechanical device 122 separates the whole stillage 120 to produce wet cake 124 (i.e., insoluble solids) and centrate 126 (i.e., liquids). The mechanical device 122 may include, but is not limited to, a centrifuge, a decanter, or any other type of separation device. The mechanical device 122 may increase solids content from about 10 to about 15% to about 25 to about 40% solids. There may be one or more mechanical devices.

The wet cake 124 are primarily solids, which may be referred to as Distillers Wet Grains (DWG). This includes, but is not limited to, protein, fiber, fat, and liquids. WDG may be stored less than a week to be used as feed for cattle, pigs, or chicken. Some of the wet cake 124 is transferred to one or more dryer(s) 128 to remove liquids. This drying produces Distillers Dried Grains (DDG) 130, which has a solids content of about 88 to 90% and may be stored indefinitely to be used as feed.

Returning to 126, the process 100 produces the centrate. The composition of the centrate 126 is mostly liquids left over from whole stillage 120 after being processed in the mechanical device 122. The process 100 sends the centrate 126, also referred to as thin stillage 132, to evaporators 134(A),(B) to boil away liquids from the thin stillage 132. This creates a thick or a concentrated syrup 136 (i.e., about 25 to about 50% dry solids) which contains soluble or dissolved solids, fine suspended solids (generally less than 50 μm) and buoyant suspended solids from fermentation.

The evaporators 134(A),(B) may represent multiple effect evaporators, such as any number of evaporators, from one to about twelve evaporators. Some process streams may go through a first effect evaporator(s) 134(A), which includes one to four evaporators and operate at higher temperatures, such as ranging to about 210° F. (about 99° C. or about 372 K). While other process streams may go through a second effect evaporator(s) 134(B), operated at slightly lower temperatures than the first effect evaporator(s) 134(A), such as ranging from about 130° F. to about 188° F. (about 54° C. to about 87° C. or about 328 K to about 360 K). The second effect evaporator(s) 134(B) may use heated vapor from the first effect evaporator(s) 134(A) as heat or use recycled steam. In other embodiments, there may be three or four effect evaporator(s), which operate at lower temperatures than the second effect evaporator(s). In embodiments, the multiple effect evaporators may range from one effect up to ten effects or more. This depends on the plants, the streams being heated, the materials, and the like. In embodiments, the evaporators may be in series or in parallel.

The process 100 sends the syrup 136 from the evaporators 134(A) to the dryer 128 to produce Dried Distillers Grain with Solubles (DDGS) 138. In some instances, the syrup 136 may be combined with wet cake 124 processed by the mechanical device 122 and sold as DDGS 138.

In another embodiment, the process 100 may send the thin stillage 132 to a process for oil recovery 140, which removes oil from the thin stillage 132 to recover oil. As a result, the process 100 produces a product of back-end oil 142 and solids 144. The process 100 may send solids, water, and the like 146 from the oil recovery 140 back to the evaporators 134(B) for further processing.

Figure 2:
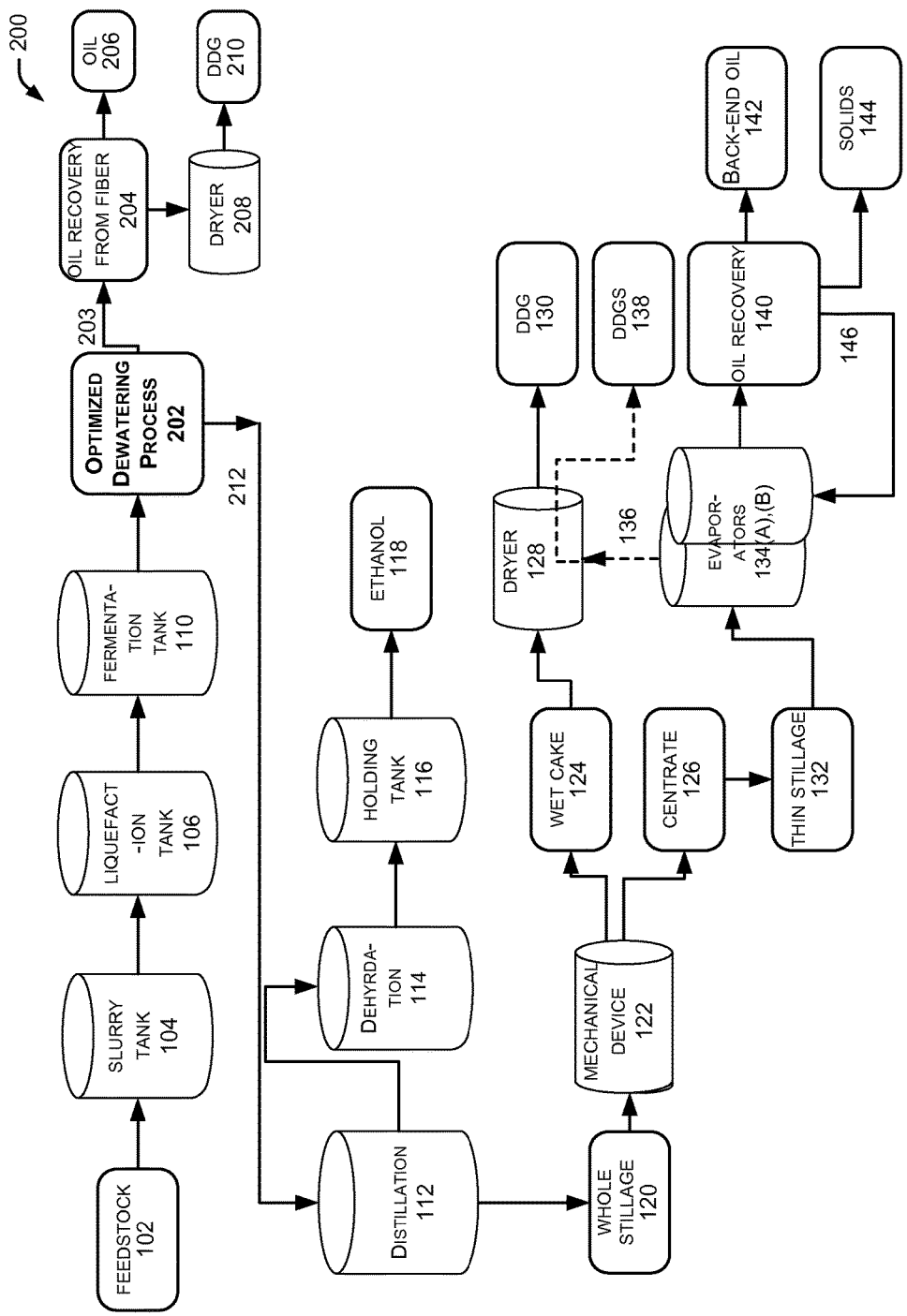
FIG. 2 illustrates an example environment for an optimized dewatering process in a middle of a production facility.

FIG. 2 is similar to FIG. 1, except this figure illustrates an embodiment of the optimized dewatering process used in the middle of the dry grind process. The process 200 illustrates the embodiment of the optimized dewatering process 202 shown after fermentation tank 110. The process 200 takes the soluble solids 203 through oil recovery from fiber 204 and recovers oil 206. Furthermore, the process 200 sends a portion from oil recovery from fiber 204 to dryer 208 to produce DDG 210. Meanwhile, the process sends the liquid with small particles 212 to distillation 112.

Figure 3:
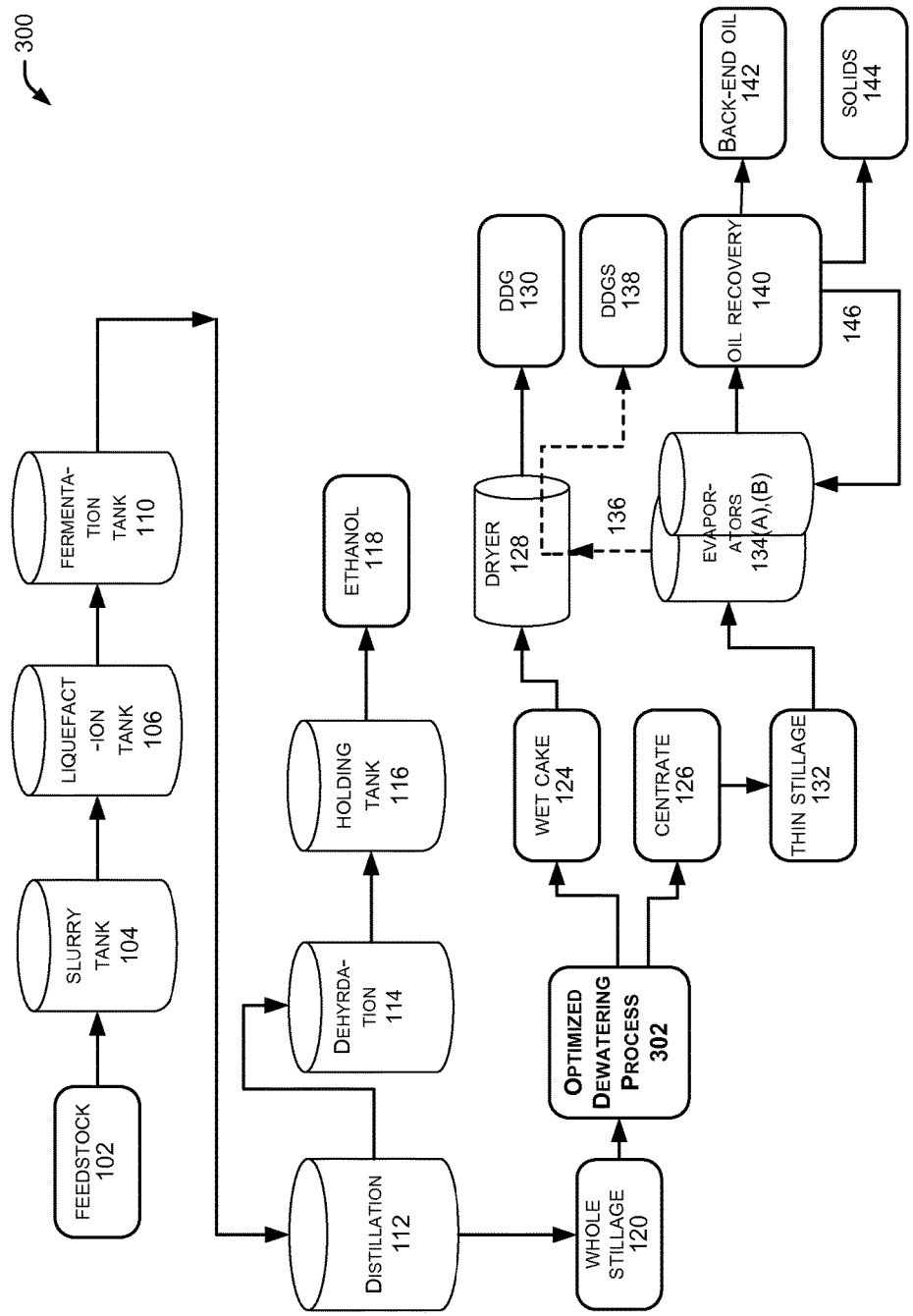
FIG. 3 illustrates another example environment for an optimized dewatering process in a back end of a production facility.

FIG. 3 is similar to FIG. 1, except this figure illustrates an embodiment of the optimized dewatering process used in the back end of the dry grind process. The process 300 illustrates the embodiment of the optimized dewatering process 302 shown after whole stillage 120.

Figure 4:
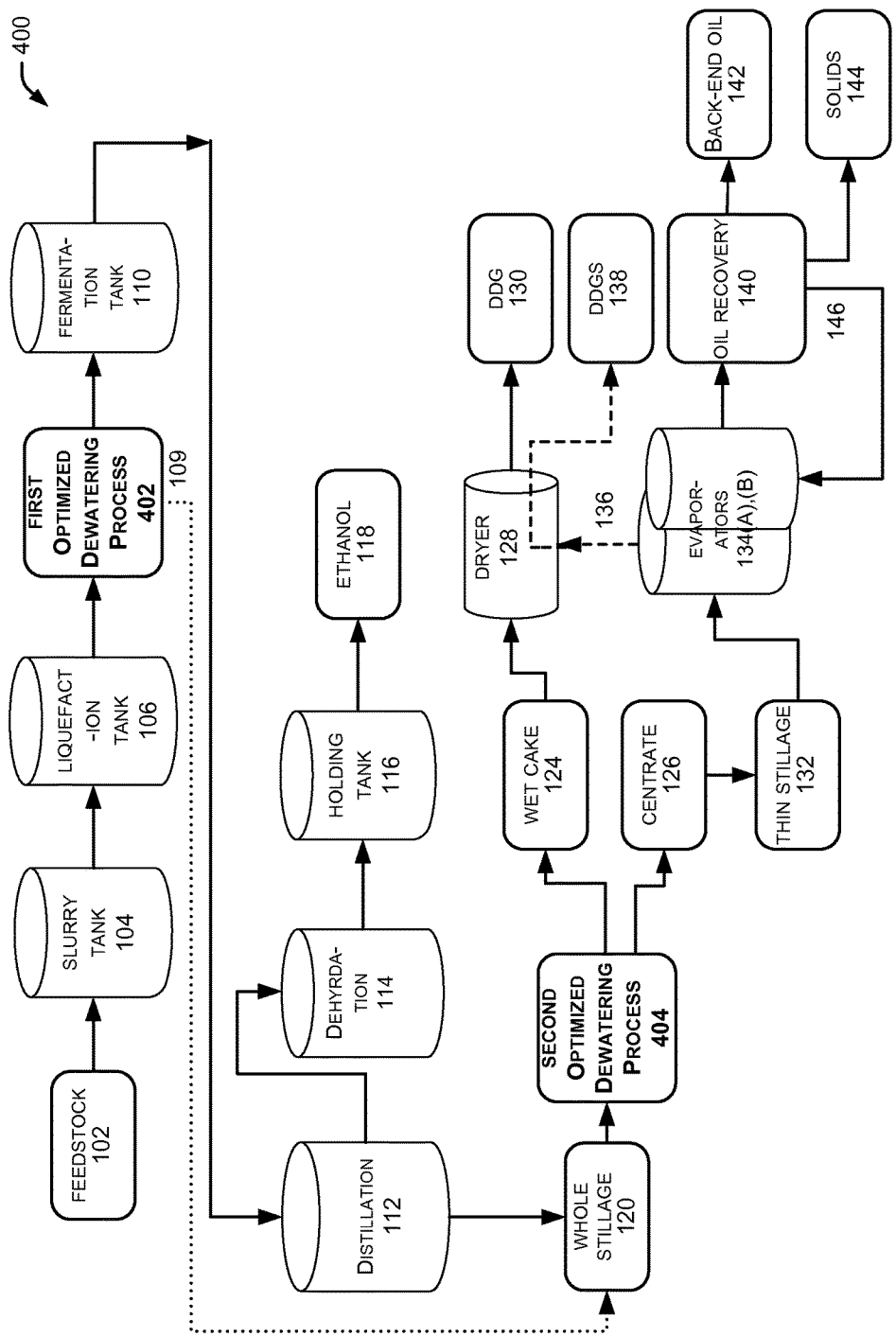
FIG. 4 illustrates another example environment for optimized dewatering processes in the front end and the back end of the production facility.

FIG. 4 is similar to FIG. 1 and FIG. 3, except this figure illustrates an embodiment of two optimized dewatering processes used in the front end and the back end of the dry grind process. The process 400 illustrates the embodiment of a first optimized dewatering process 402 and a second optimized dewatering process 404 shown after whole stillage 120.

Another embodiment (not shown) may exist, that includes three optimized dewatering processes, the first optimized dewatering process occurs after liquefaction, the second optimized dewatering process occurs after fermentation and the third optimized dewatering process occurs after whole stillage, as seen in respectively in FIGS. 1, 2, and 3.

Optimized Dewatering Processes

Figure 5:
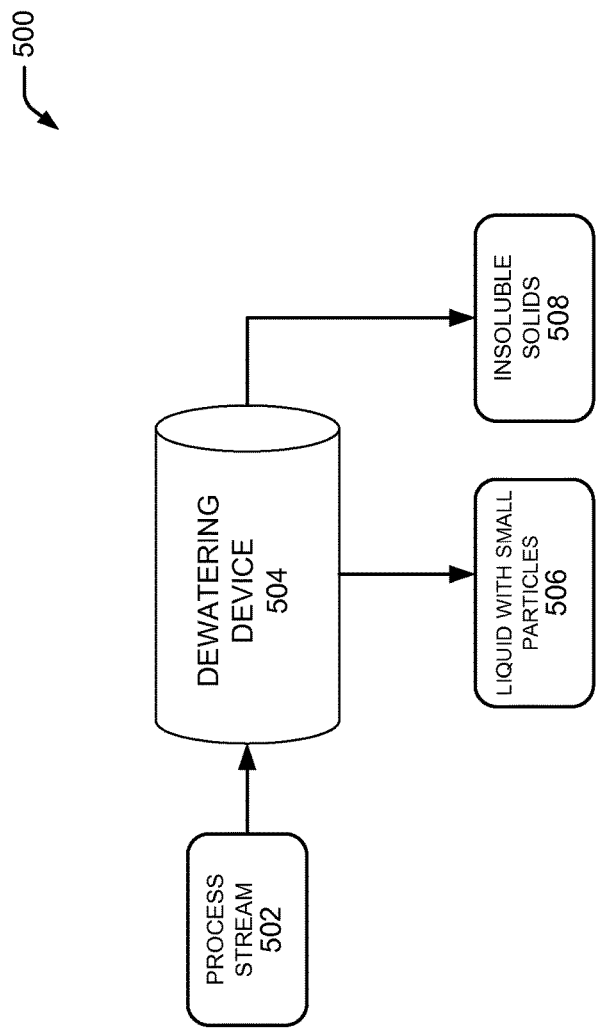
FIG. 5 illustrates an example of an optimized dewatering process with a device.

FIGS. 5-8 illustrate examples of the optimized dewatering process that may be used with the various environments described in this specification. FIG. 5 illustrates the optimized dewatering process 500 obtaining a process stream 502, such as slurry from a liquefaction tank 106. As discussed, other embodiments include, but are not limited to, the optimized dewatering process 500 obtaining a mixture, the process stream from a slurry tank, from a jet cooker, from a first or a second liquefaction tank, after a pretreatment tank in cellulosic process, any type of process streams or mixtures in any type of production facilities, and the like.

The process stream 502 may have about 15 to about 18% solids. In other embodiments, the process stream may have about 5 to about 38% solids. The process 500 uses a dewatering device 504 to create the liquid with small particles 506 stream, which may contain about 1% to 20% solids, and the insoluble solids 508, which may contain about 10% to about 70% solids content. In embodiments, the insoluble solids may have solids content that are greater than about 25% solids, greater than about 35% solids, about 40% solids, less than 45% solids, about 50% solids, less than 55% solids, and the like. The dewatering device 504 may perform using mechanical energy, by a gravity separation, and the like. The dewatering device 504 may include, but is not limited to, rotary presses, rotary thickeners, rotary vacuum-drum filters, hydrocyclones, dynamic filtering screens, static screens, dewatering screens, pressure screens, gravity DSM screens, vibration screens, screw presses, belt filter presses, continuous belt filter presses, vacuum filters, centrifuges, paddle screens, dewatering screws, gravity separators, tanks, depth filters, columns, mixer-settlers, skimmers, and the like. The type of dewatering device 504 to be used depends on factors, such as type of process streams, liquid and solid goals at start and at end of process, the type of solids, desired reduction of carbon intensity, desired reduction of GHG emissions, and the like.

In an embodiment, the dewatering device 504 includes a screen. Screens may be made with different thicknesses of wire, the thicker the wires, the smaller the particle size passing through that screen, and vice versa. A micron is a measurement for measuring particle size. A micron is one-millionth of a meter or one twenty-five thousandth of an inch. The screen may range from about 10 microns to about 800 microns in size. In an embodiment, the dewatering device 504 uses 150 microns size screen to filter particles that are greater than 300 microns in size. Thus, particles that are smaller than 300 microns will travel through the screen as filtrate while particles greater than 300 microns will not travel through the screen, but will be collected as solids. In another embodiment, the dewatering device 504 uses a 100 microns size screen to filter particles that are greater than 200 microns in size. In yet another embodiment, the dewatering device uses a 200 microns size screen to filter particles that are greater than 400 microns in size.

For instance, the optimized dewatering process 500 may increase the concentration of the solids content from 35% solids content without the optimized dewatering process, to 45% solids content with the optimized dewatering process for insoluble solids. As a result, the amount of natural gas and electricity used for evaporating and/or drying the insoluble solids is greatly reduced, and the amount of GHG and/or carbon emissions from the evaporators and dryers are reduced as well.

The dewatering device 504 may press the slurry to force liquid with small particles 506 (i.e., the water, starch, gluten, and other components) through the 150 microns size screen while preventing the insoluble solids 508 (i.e., fiber) that are larger than 300 microns in size from passing through the screen. The process may use the fiber to produce Distillers Wet Grains with Solubles (DWGS) or Distillers Dried Grains with Solubles (DDGS).

After the process 500 filters the insoluble solids 508 from the process stream 502, some starch, gluten, and other components may still be with the fiber. Thus, the dewatering device 504 may include an option to spray wash the insoluble solids 508 to remove the additional amounts of starch, gluten, and/or other components. The process 500 may include a spray feature to direct a liquid medium at the insoluble solids 508. The process may adjust the liquid medium, such as wash water or solvent, based on the type of insoluble solids, type of mixture, temperature, pH, and other factors.

In another embodiment, the dewatering device 504 may include an option to add liquid medium to mix the insoluble solids 508 in order to remove the additional amounts of starch, gluten, and/or other components. The dewatering device 504 may add the liquid medium, such as wash water, to the insoluble solids 508 and send the wash water with the insoluble solids 508 through the dewatering device to separate the insoluble solids 508 from the wash water, which contains the additional starch, gluten, and other components from the fiber. The wash water step may occur initially, may occur in a second stage, or may occur in multiple stages. In embodiments, there may be one to five, or more stages of washing. The liquid medium may include, but is not limited to, cook water, clean water, recycle water, wash water, alcohol, methanol, butanol, ethanol, and the like.

The optimizing dewatering process 500 may use a direct displacement that uses water in the process more efficiently. For instance, displacement occurs when an object is immersed in a liquid medium, pushing it out of the way and taking its place. Here, the optimizing dewatering process 500 measures the volume of the liquid medium being displaced, and determines the volume of an immersed object. In this example, the volume of the insoluble solids 508 may be exactly equal to the volume of the displaced liquid medium.

In an embodiment, the optimized dewatering process 500 uses a rotary press to separate components in the mixture of liquids and solids, such as separating the insoluble solids from the liquid with small particles stream. The rotary press includes a dewatering unit with a 3-inch channel, screen, gear unit, feed inlet, motor, filtrate discharge, and solids discharge. The rotary press receives the mixture between two parallel filtering elements in the channel. The rotary press rotates the mixture between the two parallel filtering elements to pass filtrate, the liquid with small particles 506, through the filtrate discharge while the insoluble solids 508 advance with the channel. The rotary press dewaters the mixture as it travels around the channel. The rotary press generates back pressure to dewater the mixture and extrude the insoluble solids 508 through the solids discharge. Any type or size of rotary press may be implemented in this process, the one described above is an example of one.

In another embodiment, the rotary press includes a wash feature. The wash feature includes spraying wash water on the mixture as it enters the 3-inch channel. The wash feature may be used initially during the dewatering or may be used in a second stage of dewatering. The wash feature helps remove starch and protein that may still be with the fiber. The insoluble solids may contain about 10% to about 70% solids content and have particles that are greater than 300 microns in size. The results are further discussed under the Examples of Test Results Section.

Figure 6:
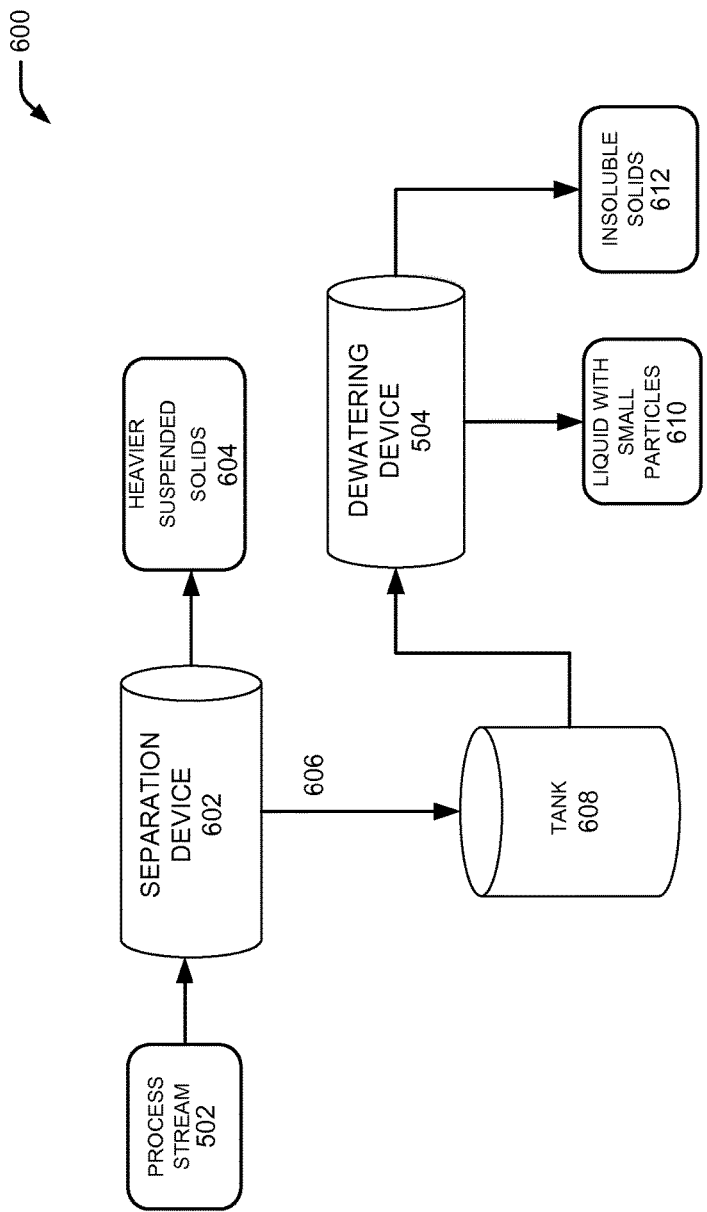
FIG. 6 illustrates another example of an optimized dewatering process with two devices.

FIG. 6 is similar to FIG. 5, except this figure illustrates an embodiment of the optimized dewatering process 600 used with a separation device 602 and the dewatering device 504. Details that are not similar to FIG. 5 will be discussed below with reference to FIG. 6. The separation device 602 separates heavier, lighter, larger, or smaller suspended solids 604 from the process stream 502 to create a liquid with insoluble solids stream 606. The separation device separates the suspended solids based on density, particle size, and the like. The suspended solids 604 may be further processed, sent through the separation device again, or sent to the dryer 128. The separation device 602 may include, but is not limited to, centrifuge, paddle screen, or any type of dynamic or static mechanical processor that separates out large size particles from small size particles, heavier suspended solids from other lighter solids, solids from liquids, and the like.

In an embodiment, the optimized dewatering process 600 further sends the liquid with solids stream 606 to a tank 608. While in another embodiment, there is no tank, so the liquid with solids stream 606 goes directly to the dewatering device 504. The optimized dewatering process 600 creates the liquid with small particles 610 stream, which will be sent to the fermentation tank 110 and the insoluble solids 612, which may be sent to the dryer 128. The insoluble solids 612 may contain about 10% to about 70% solids content and have particles that are greater than 20 microns in size.

In an embodiment, the separation device may be a paddle screen while the dewatering device may be a rotary press. In another embodiment, the separation device may be a centrifuge and the dewatering device may be a rotary press.

In yet another embodiment, the separation device 602 may be a paddle screen and the dewatering device 504 may operate by using static gravity separation. Static gravity separation is efficient at separating one component, the insoluble solids from the other components by gravity. This is possible due to all of the components of the mixture (i.e., process stream) having different specific weights. The static gravity separation methods use gravity as a dominant force to separate out the components. For instance, the static gravity separation separates the components based on the characteristic of the process stream, such as density. Advantages of using the static gravity separation include low capital and operating costs.

Figure 7:
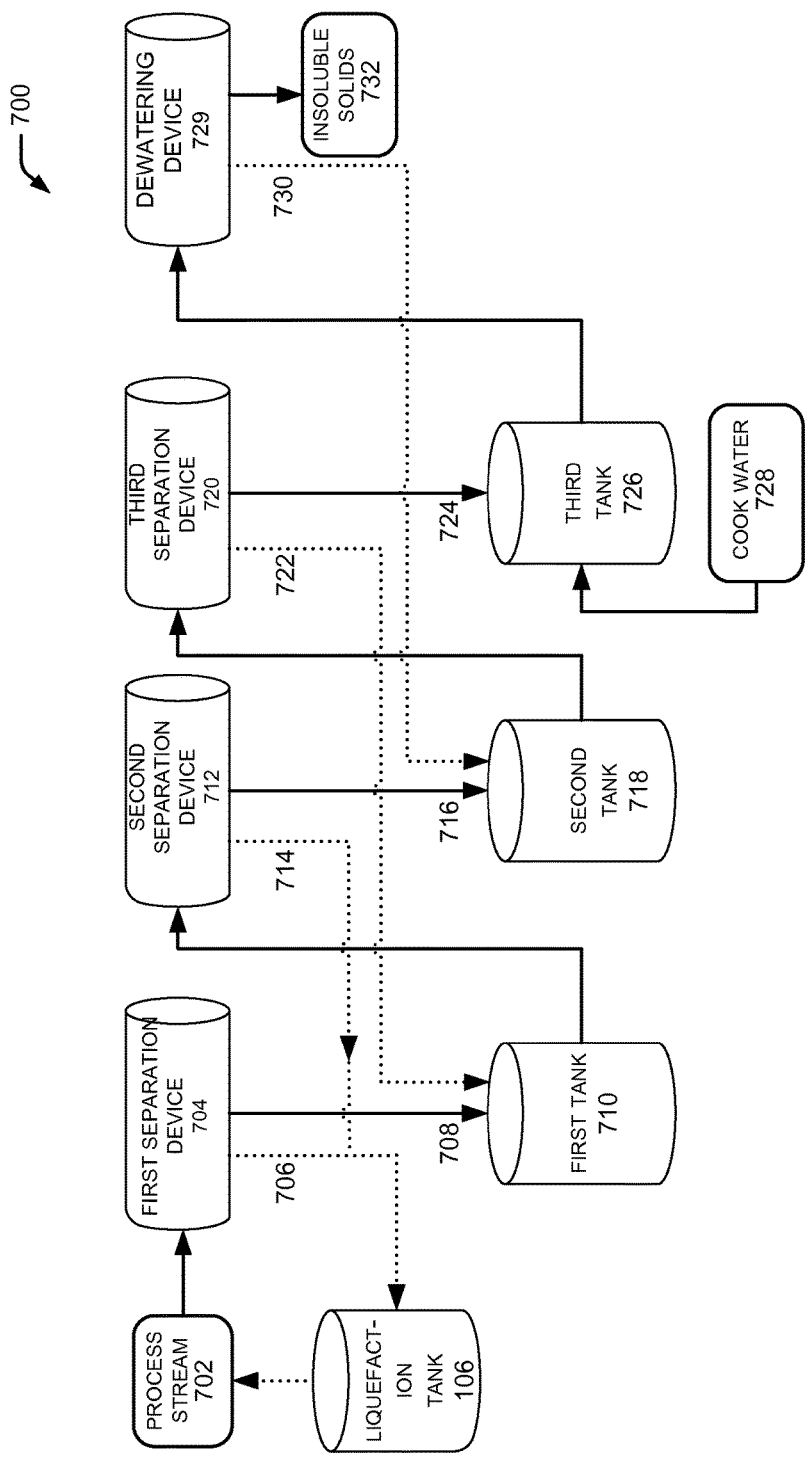
FIG. 7 illustrates another example of an optimized dewatering process with multiple devices.

FIG. 7 illustrates an example of the optimized dewatering process with multiple devices. For illustrative purposes, the liquid with small particles streams are shown in dotted lines. The optimized dewatering process 700 uses three separation devices, such as a first separation device, a second separation device, a third separation device, and the dewatering device. In an embodiment, a paddle screen is used where the screen has openings that are sized to allow water, starch, and smaller sized particles to flow through the screen but will not allow the larger particles, such as fiber to flow through. The size screens may range from 10 microns size screen to about 800 microns size screen. Thus, the screen filters particles ranging from 10 microns to 1600 microns in size. In embodiments, the size screen may range from 50 microns size screen to about 500 micron size screen. Thus, the screen filters particles ranging from 100 microns to 1000 microns in size.

The optimized dewatering process 700 may use a counter-flow wash where a first pass occurs with the first separation device 704 creating a first liquid with small particles 706 (i.e., starch, gluten, protein, salt, and the like) stream to pass through the screen and sent to a liquefaction tank 106, which makes the process stream 702 (as shown by the dotted line). The first separation device 704 also produces first large solids 708. However, the first large solids 708 may still contain starch and/or protein, so it goes to a first tank 710 where a third liquid with small particles stream 722 are added in the first tank 710, and the process 700 sends this mixture through the second separation device 712.

The second separation device 712 produces a second liquid with small particles stream 714 and a second large solids 716 from the mixture. The optimizing dewatering process 700 sends the second liquid with small particles 714 stream to liquefaction tank 106 and sends the second large solids 716 to the second tank 718 where liquids 730 are added to the second tank 718. Again, the second large solids 716 may still contain starch and/or protein, so the process 700 sends it through the third separation device 720.

The third separation device 720 produces the third liquid with small particles stream 722 and a third large solids 724. The optimizing dewatering process 700 sends the third liquid with small particles stream 722 to the first tank 710 and sends the third large solids 724 to the third tank 726 where cook water 728 is added in the third tank 726.

Next, the dewatering device 729 receives the mixture of the third large solids 724 with cook water 728 to create liquids 730 and insoluble solids 732. The process 700 sends the liquids 730 to the second tank 718 and the insoluble solids 732 may be used to produce DWGS or DDGS.

Any number of separation devices may be used, ranging from one to five or more devices used in combination with the dewatering device. The optimized dewatering process may increase the solids content from about 35% without the optimized dewatering process to about 50% with the optimized dewatering process. This helps reduce the amount of energy needed for downstream processing, such as evaporation and drying. Furthermore, this helps improve with drying throughput and increases the dryer process capacity.

Figure 8:
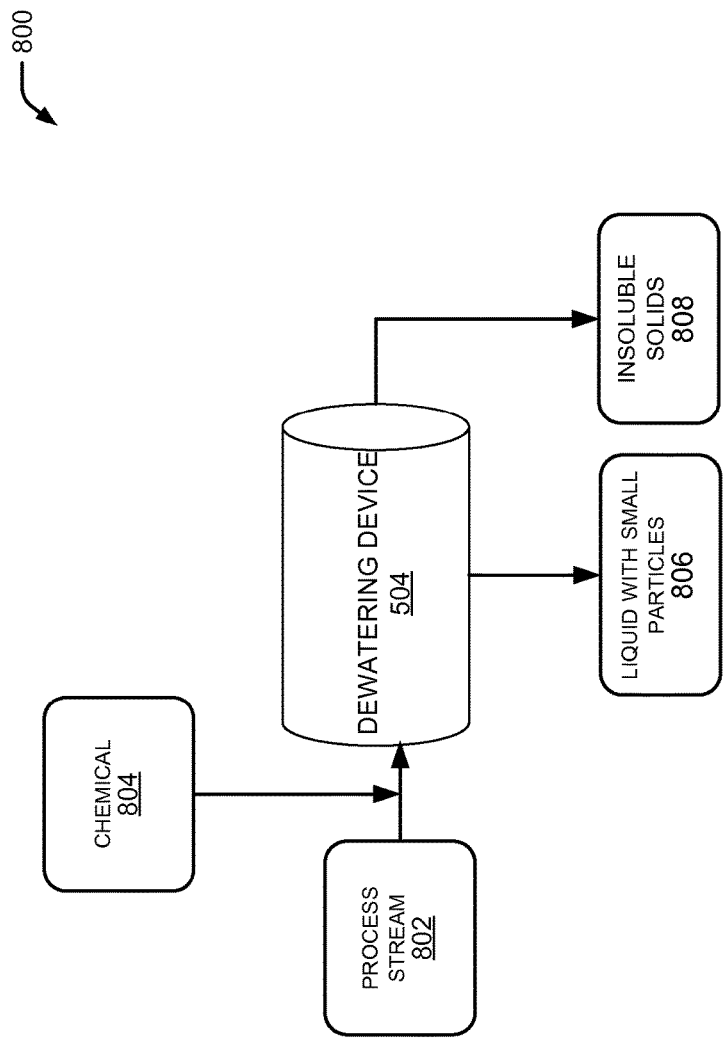
FIG. 8 illustrates another example of an optimized dewatering process with a chemical and a device.

FIG. 8 illustrates another example of an optimized dewatering process 800 with a chemical and a device. The chemical 804 may reduce the surface tension of water and may reduce the viscosity. The chemical 804 may include, but is not limited to surfactants, such as wetting agents, emulsifiers, foaming agents, dispersants, and the like. The surfactant contains a water insoluble (or oil soluble) component and a water soluble component. The surfactant may diffuse in water and adsorb at interfaces between air and water or at the interface between oil and water, in the case where water is mixed with oil.

The chemical used is GRAS approved, meaning it satisfies the requirements for the United States' FDA category of compounds that are "Generally Recognized as Safe." Since the chemical is GRAS approved, it does not need to be removed and may be included in the distiller grains and be fed to livestock and/or other animals when used within the dosage and application guidelines established for the particular product formulation. Also, the chemical may be considered a processing aid under the government agencies, such as the U.S. Food and Drug Administration, the Center for Veterinary Medicine, and the Association of American Feed Control Officials based on their standards.

The process 800 adds an effective amount of the chemical 804 to the process stream 802 in an inline static mixer or in a tank. Other possible ways of adding the chemical include, but are not limited to fed into a clarifier, a thickener feedwell, and the like. A dosage amount of chemical 804 may range from about 10 to about 10,000 parts per million (ppm). Another dosage may be used in concentrations of about 0.05% to about 10% chemical 804 according to standard practices. The chemical 804 may be added at varying concentrations, at different stages of the process, and the like. The dosage amount of chemical 804 depends on viscosity reduction desired, type of device used, and the like.

The process 800 sends the mixture of process stream 802 with chemical 804 through the dewatering device 504 to create the liquid with small particles 806 stream and the insoluble solids 808.

Other Illustrative Environments

Figure 9:
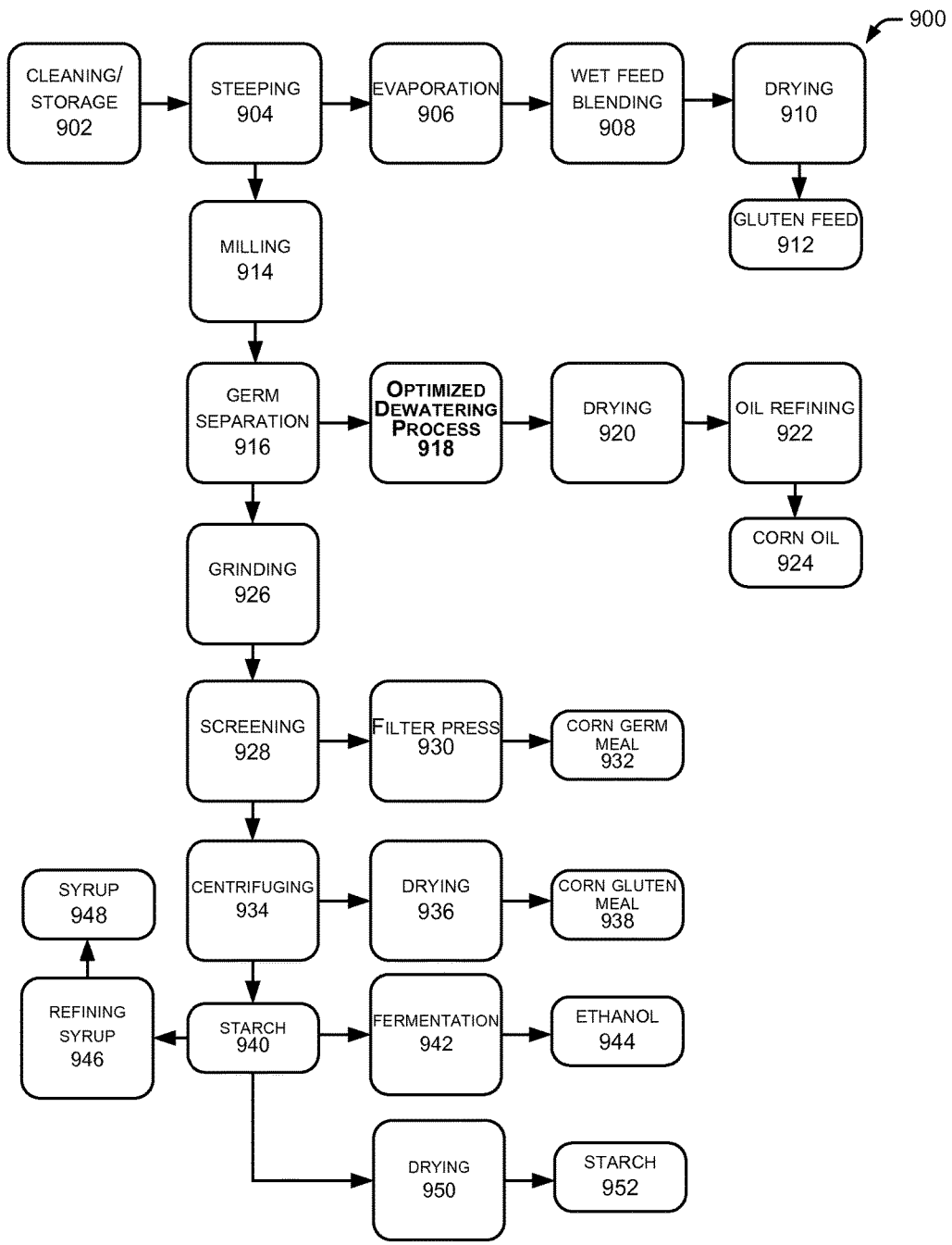
FIG. 9 illustrates an example environment for an optimized dewatering process after germ separation in a production facility.
Figure 10:
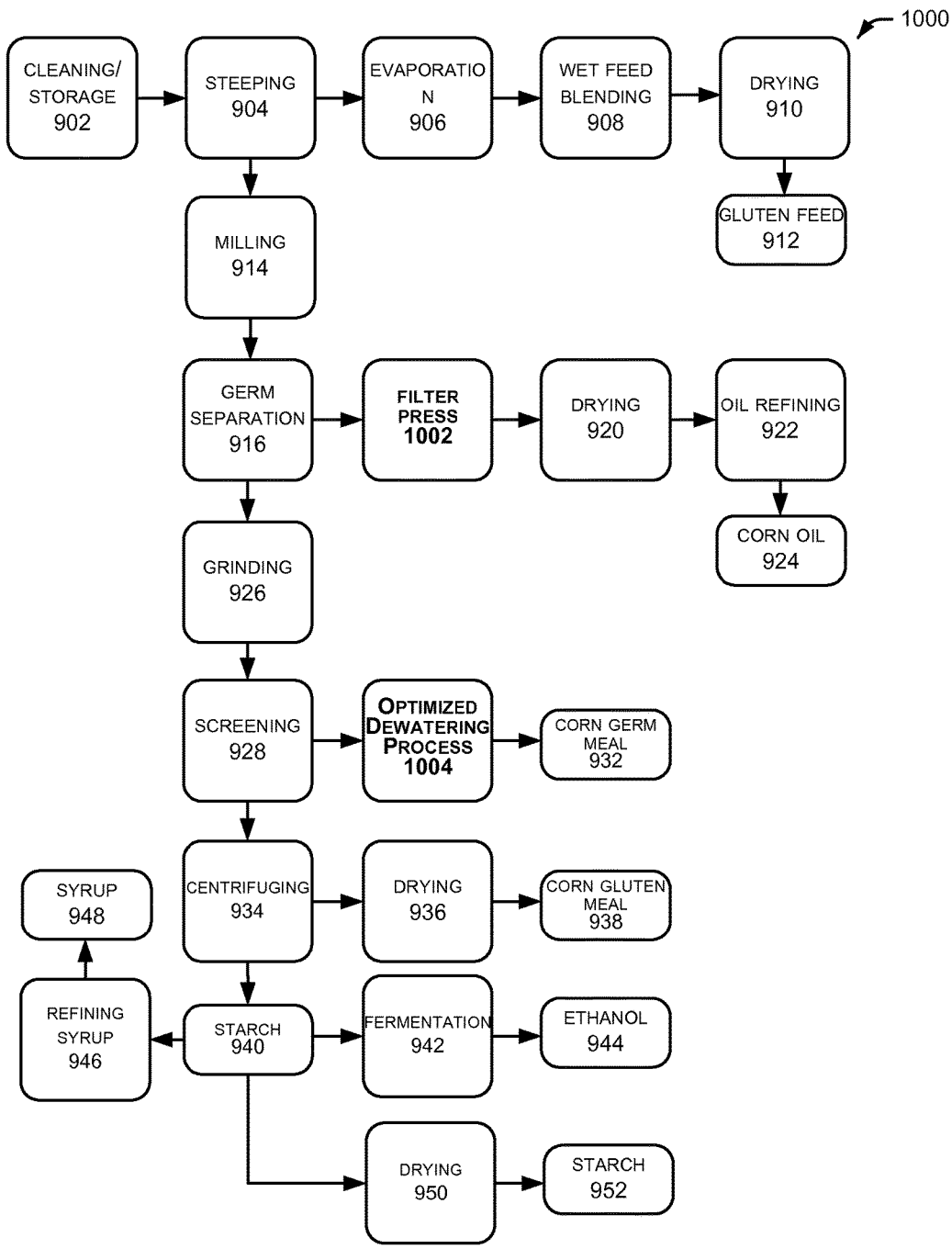
FIG. 10 illustrates another example environment for an optimized dewatering process after screening in the production facility.
Figure 11:
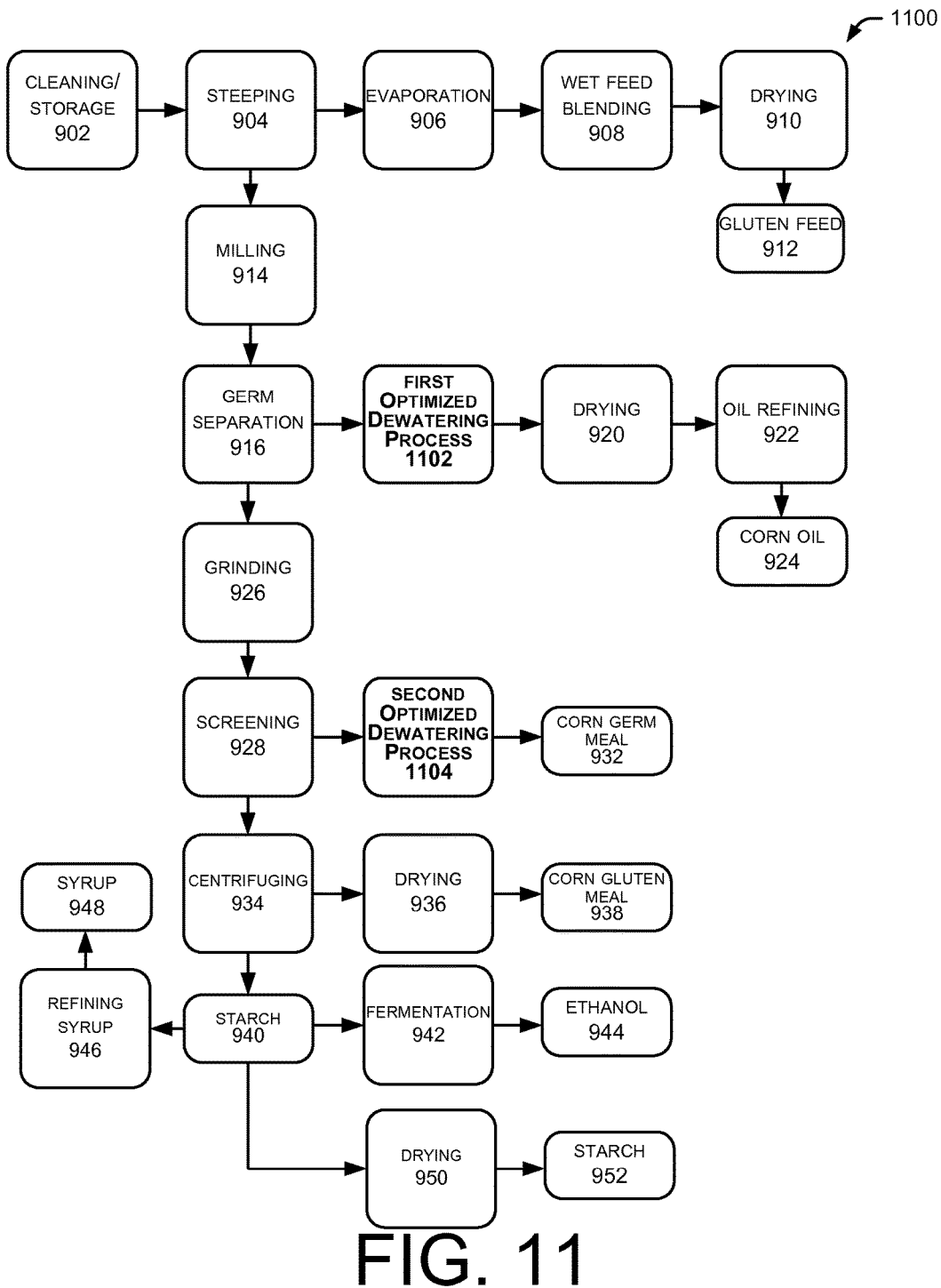
FIG. 11 illustrates another example environment for optimized dewatering processes after germ separation and after screening in the production facility.

FIGS. 9-11 are flow diagrams showing example environments that may be used with the optimized dewatering process. FIG. 9 illustrates the wet mill process which converts corn into several different co-products, such as gluten feed (high fiber animal feed), germ (corn oil), meal, gluten meal (high protein animal feed), starch-based products such as ethanol, high fructose corn syrup, and starch.

In an example, the process 900 starts with cleaning/storage 902 of corn. The process carefully dries and stores the corn without exposure to temperatures above 80° C. The process 900 proceeds to steeping 904 by soaking the corn in water and sulfur dioxide for 24 to 48 hours to soften the kernels. The process 900 sends the solids, which are at 5-10% solids content and contain 43-45% protein from steeping 904 to evaporation 906 in which the process 900 removes water to increase the solids to 40-50% content.

Next, the process 900 completes wet feed blending 908 where the steep liquor is mixed with corn fiber. Then the process 900 sends the wet feed blending 908 to drying 910 to be processed into gluten feed 912.

Returning to steeping 904, the process 900 sends the steeped corn and water to milling 914 in which the corn is coarsely ground to open the kernels and to break the grain so the germs can be separated with little damage. The process 900 sends this to germ separation 916 where cyclones (i.e., hydrocyclones) separate oil-bearing germs based on density. The hydrocyclones use swirling motion to force heavier particles (i.e., germ-lean materials) against the wall and exit out the bottom port while the lighter particles (i.e., germ-rich materials) exit out the top. The germ-rich materials go through a series of washes to wash the germs from the materials.

Next, the optimized dewatering process 918 dewaters the washed germ-rich materials (i.e., the germs) from the liquid. The optimized dewatering process 918 may be any of the embodiments described with reference to FIGS. 5-8. The process 900 sends the germ that is separated to drying 920, for oil refining 922 to be be sold as corn oil 924.

The germ-lean materials may go through another mill, grinding 926 to release more germs, now referred to as degermed corn slurry. The process 900 sends the degermed corn slurry, which includes fiber, starch, and gluten for screening 928. The screening 928 may use Dutch State Mines screen (50 μm opening wedge wire, 120° wire concave) to separate the fiber from the starch and the gluten by washing the degermed corn slurry. The washed fiber contains about 10%-15% solids. The process may use a filter press 930 to dewater the washed fiber Next, the process 900 may mix the dewatered fiber with evaporated steepwater, dry the blend, pellet the blend and sold as gluten feed 912 or add germ meal to be sold as corn germ meal 932.

Turning to centrifuging 934, the process 900 separates the gluten from the starch. The centrifuging 934 may use disk-nozzle type centrifuges to obtain high-protein gluten which is sent to drying 936 to be sold as corn gluten meal 938.

The starch 940 from the centrifuging 934 goes through fermentation 942 to produce ethanol 944. In some instances, the $CO_2$ from fermentation 942 is recovered and sold as a commodity product. One of having ordinary skill in the art understands the specifics of the fermentation 942 process in the wet mill process. Steps of distillation and dehydration may be included after fermentation. These steps will not be discussed here.

The starch 940 may undergo refining syrup 946 to produce syrup 948. Furthermore, the starch 940 may go to drying 950 and sold as starch 952. It will be understood by one having ordinary skill in the art that the above wet mill process may be manipulated and modified as desired.

FIG. 10 is similar to FIG. 9, except this figure illustrates an embodiment of the optimized dewatering process used after screening in the wet grind process. The process 1000 illustrates a filter press 1002 used after germ separation 916 and the embodiment of the optimized dewatering process 1004 shown after screening 928.

FIG. 11 is similar to FIG. 9 and FIG. 10, except this figure illustrates an embodiment of two optimized dewatering processes used after germ separation 916 and after screening 928 of the dry grind process. The process 1100 illustrates the embodiment of a first optimized dewatering process 1102 and a second optimized dewatering process 1104. The optimized dewatering processes shown in FIGS. 9-11 may be any of the embodiments described with reference to FIGS. 5-8.

The University of Nebraska collected data for GHG emissions from a natural gas ethanol production facility in Iowa. The emissions are expressed as $CO_2$ equivalents, shown below. See, Don Hafstrand, "Greenhouse Gas Emissions of Corn Ethanol Production, " Agricultural Marketing Resource Center Renewable Energy Newsletter, August 2009.

| Greenhouse Gas Emissions from Iowa Plant | | |
|---|---|---|
| Production Facility | Emissions per Unit of Energy Produced* | Percent |
| Natural Gas | 19.7 | 34% |
| Electricity | 6.5 | 11% |
| Depreciation Capital | 0.5 | 1% |
| Grain Transport | 2.1 | 4% |
| Total | 28.8 | 50% |

*Grams of $CO_2$ equivalent emissions per megajoule of energy produced.

Fifty percent of the emissions generated are from growing corn and the other fifty percent of emissions generated are from processing the corn to produce ethanol. The emissions from natural gas are approximately 34% and emissions from electricity are 11%, which is about 90 percent of the emissions from the production facility. The optimized dewatering process provides opportunities to reduce the amount of natural gas and electricity used in processing grain to produce alcohol, and thus reducing the amount of emissions.

Another table showing data from California Air Resources Board show emissions for dry mills and wet mills. See, California Environmental Protection Agency, Air Resources Board, "Detailed California-Modified GREET Pathway for Corn Ethanol, " Jan. 20, 2009, v. 2.0.

| Greenhouse Gas Emissions from Dry Mill and Wet Mill | | |
|---|---|---|
| Corn Ethanol Fuel Cycle Components | Dry Mill GHG (g$CO_2$/MJ) | Wet Mill GHG (g$CO_2$/MJ) |
| Ethanol Production | 38.3 | 48.78 |
| Chemical Inputs to Cultivation | 30.2 | 31.35 |

This data reflects direct emissions only for producing ethanol for the dry mill and wet mill. There are opportunities to reduce these emissions using the optimized dewatering process in processes for dry mill and wet mill.

Yet another table showing data from California Air Resources Board show energy used to produce ethanol for dry mills and wet mills.

| Ethanol Production Energy Use from Dry Mill and Wet Mill | | |
|---|---|---|
| Fuel Type | Dry Mill | Wet Mill |
| Natural Gas (Btu/gal) | 34,598 | 29,613 |
| Electricity (Btu/gal) | 10,926 | 18,689 |
| Energy from EtOH (Btu/gal) | 63,983 | 63,983 |
| Total energy input for EtOH production (Btu/gal) | 109,507 | 117,554 |
| Total energy input for EtOH production (Btu//mmBtu) | 1,434,648 | 1,540,080 |

This data reflects energy use for producing ethanol for the dry mill and wet mill. There are opportunities to reduce the amount of energy by using the optimized dewatering process in processes for dry mill and wet mill.

Examples of Test Results

The optimized dewatering process was replicated in a pilot plant based on using a mixture of liquids and solids as the process stream and used with a rotary press as the dewatering device. The temperature of the mixture was 165° F., and pH was 6.87.

TABLE I

| Optimized Dewatering Process Data Without Wash | | |
|---|---|---|
| Run No. | Filtrate (%) | Solids (%) |
| 1 | 0.10 | 42.3 |
| 2 | 0.05 | 41.0 |
| 3 | 0.10 | 43.7 |
| 4 | 0.11 | 42.3 |
| 5 | 0.08 | 41.5 |
| 6 | 0.03 | 41.4 |
| 7 | 0.07 | 41.6 |
| 8 | 0.08 | 42.1 |
| 9 | 0.05 | 43.6 |
| 10 | 0.07 | 43.6 |
| Average | 0.07 | 42.3 |

Table I. indicates the data collected in the pilot plant runs. Table I shows in a first vertical column different runs, numbered as 1-10, and shows in a first row, Filtrate (%) and Solids (%). The data illustrates solids ranging from 41% to 43.6%. The rotary press was used without wash water. The data shows an average of 0.07% filtrate (i.e., liquid with small particles stream) and an average of 42.3% solids (i.e., insoluble solids).

Another data set of 20 samples using the rotary press without wash was generated. The data set showed an average of 0.12% for filtrate and 39.91% for solids.

Yet another set of runs was completed using the optimized dewatering process in the pilot plant. The set of runs used a mixture of liquids and solids as the process stream with the rotary press without wash water. The temperature of the mixture was 167° F., and pH was 6.87. Table II. below indicates the data collected in the pilot plant runs.

TABLE II

| Optimized Dewatering Process Data without Wash | | |
|---|---|---|
| Run No. | Filtrate (%) | Solids (%) |
| a | 0.01 | 43.2 |
| b | 0.06 | 43.9 |
| c | 0.09 | 42.8 |
| d | 0.10 | 41.5 |
| e | 0.10 | 42.0 |
| Average | 0.07 | 42.7 |

The data illustrates solids ranging from 41.5% to 43.9%. The data shows an average of 0.07% filtrate (i.e., liquid with small particles stream) and an average of 42.7% solids (i.e., insoluble solids).

Another set of runs was completed using the optimized dewatering process in the pilot plant. The set of runs used a mixture of liquids and solids as the process stream with the rotary press run with wash water. The temperature of the mixture was 167° F., pH was 6.87. Table III. below indicates the data collected in the pilot plant runs.

TABLE III

Optimized Dewatering Process Data with Wash

| Run No. | Filtrate (%) | Solids (%) |
|---|---|---|
| g | 0.02 | 42.7 |
| h | 0.21 | 40.8 |
| i | 0.07 | 41.0 |
| j | 0.08 | 37.9 |
| k | 0.07 | 37.4 |
| Average | 0.09 | 40.0 |

The data illustrates solids ranging from 37.4% to 42.7%. The data shows an average of 0.09% filtrate (i.e., liquid with small particles stream) and an average of 40% solids (i.e., insoluble solids). Data showing the composition of the solids would indicate whether the washing helped remove the starch and gluten from the fiber.

Although the subject matter has been described in language specific to structural features and/or methodological acts, it is to be understood that the subject matter defined in the appended claims is not necessarily limited to the specific features or acts described. Rather, the specific features and acts are disclosed as example forms of implementing the claims.

What is claimed is:

1. A method of reducing an amount of energy needed for processing streams in an agricultural production facility, the method comprising:
   receiving a process stream of grain components, the process stream including a mixture of liquids and suspended solids;
   separating the suspended solids from the liquids using a paddle screen to form a liquid with insoluble solids stream; and
   dewatering the liquid with the insoluble solids stream post liquefaction by using a rotary press to produce 1) a liquid with particles stream and 2) insoluble solids, which have a solids content of about 10% to about 70% solids.

2. The method of claim 1, wherein the process stream is obtained as a slurry from a liquefaction tank.

3. The method of claim 1, wherein the insoluble solids have particle sizes that range from about 20 microns to about 1000 microns.

4. The method of claim 1, further comprising drying the suspended solids.

5. The method of claim 1, further comprising sending the liquid with particles stream to fermentation.

6. The method of claim 1, further comprising sending the insoluble solids to be processed and to sell as a feed product, or sending the insoluble solids to be processed and mixed with syrup to sell as a feed product with syrup.

7. The method of claim 1, further comprising sending the insoluble solids through a mechanical device to be further separated.

8. A method of reducing an amount of energy needed for processing streams in an agricultural production facility, the method comprising:
   receiving liquids and suspended solids in a process stream from the agricultural production facility; and
   dewatering the liquids and suspended solids in the process stream post liquefaction using a rotary press to produce 1) a liquid with particles stream and 2) insoluble solids having a solids content of greater than about 25% solids.

9. The method of claim 8, wherein the liquids and suspended solids in the process stream comprise about 10% to about 38% solids content.

10. The method of claim 8, wherein the liquid with particles stream comprises solids up to about 20% solids content.

11. The method of claim 8, further comprising drying the insoluble solids having solids content greater than about 25%.

12. The method of claim 8, further comprising separating the suspended solids from the liquids using a paddle screen prior to the dewatering.

13. A method comprising:
   receiving liquids and solids in a process stream up to about 38% solids content; and
   dewatering the liquids and solids in the process stream post liquefaction using a rotary press to produce 1) a liquid with particles stream having up to about 20% solids content and 2) insoluble solids having less than about 55% solids content.

14. The method of claim 13, further comprising adding a chemical to the liquids and solids in the process stream prior to the dewatering.

15. The method of claim 13, further comprising adding a liquid medium to the insoluble solids to remove additional components.

16. The method of claim 13, further comprising spray or submerge washing the insoluble solids to remove additional amounts of components.

17. The method of claim 13, further comprising separating the suspended solids from the liquids using a paddle screen prior to the dewatering.

* * * * *